United States Patent [19]

Curtze et al.

[11] Patent Number: 4,912,217
[45] Date of Patent: Mar. 27, 1990

[54] PREPARATION OF 3,3-DIPHENYLACRYLIC ACID AMIDES

[75] Inventors: Jurgen Curtze, Johannisberg; Günter Krummel, Mainz, both of Fed. Rep. of Germany

[73] Assignee: Shell Internationale Research Maatschappij B.V., The Hague, Netherlands

[21] Appl. No.: 347,273

[22] Filed: May 4, 1989

[30] Foreign Application Priority Data

May 25, 1988 [DE] Fed. Rep. of Germany ....... 3817711

[51] Int. Cl.$^4$ .................. C07C 103/58; C07C 102/00; C07D 295/18
[52] U.S. Cl. .................................... 544/158; 534/588; 544/159; 544/165; 544/176; 564/162; 564/167; 564/168; 564/171; 564/172; 564/174; 564/180; 564/181

[58] Field of Search ................ 534/588; 544/158, 159, 544/165, 176; 564/162, 167, 168, 171, 172, 174, 180, 181

[56] References Cited

U.S. PATENT DOCUMENTS 4,753,934 6/1988 Nickl ................................ 514/231.5

FOREIGN PATENT DOCUMENTS 208999 1/1987 European Pat. Off. .
219756 4/1987 European Pat. Off. .
294907 12/1988 European Pat. Off. .

Primary Examiner—Mary C. Lee
Assistant Examiner—M. S. Howard

[57] ABSTRACT 3,3-diphenylacrylic acid amides are prepared by the reaction of a benzophenone with an acetamide in the presence of an alkali metal tertiary alcoholate characterized in that an alkali metal mono-alkyl carbonate is additionally present.

9 Claims, No Drawings

PREPARATION OF 3,3-DIPHENYLACRYLIC ACID AMIDES

The present invention relates to an improved process for the preparation of 3,3-diphenylacrylic acid amides.

EP0 120 321 A1, EP 0 208 999 A1 and EP 0 219 756 A1 disclose certain 3,3-diphenylacrylic acid amides and various methods for the preparation of such compounds. These compounds exhibit fungicidal activity and are particularly suitable for the control of phytopathogenic fungi. EP 0 294 907 discloses a different method for the preparation of such compounds which involves the reaction of a benzophenone with an appropriate acetamide in the presence of a strong base and European Patent Application No. 89200378.1 reveals that the yield of this reaction is improved if a sodium tertiary alcoholate is used as the base. However, such alcoholates react readily with the water which is produced in the course of the reaction yielding the corresponding alcohol and alkali metal hydroxide. This hydroxide in turn cleaves base-sensitive reactants, such as the acetamide or the desired product, often to a large extent and thus reduces the yield from the process. Attempts to overcome this problem heretofore have involved the use of a substantial excess, generally 3-fold or even higher, of the acetamide reactant. However, such processes still yield a product of less than 90% purity.

It has now been found that, surprisingly, the cleavage side reaction can be suppressed by the addition of an alkali metal mono-alkyl carbonate thereby reducing the need for excess acetamide reactant to only a small excess, e.g. a 1.5 fold excess, and increasing the purity of the products to nearly 100%.

According to the present invention there is therefore provided a process for the preparation of a 3,3-diphenylacrylic acid amide of general formula I $$\underset{B}{\overset{A}{>}}C=CH-COQ \qquad (I)$$

wherein
A represents

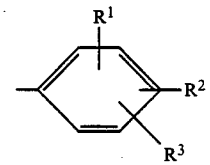

B represents

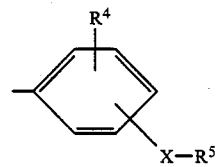

Q represents

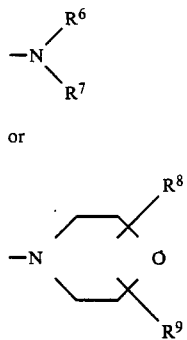

or

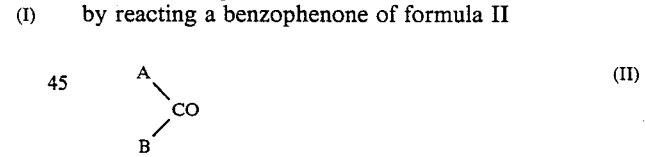

in which
$R^1$ is $C_{1\text{-}4}$alkyl, $C_{1\text{-}4}$-alkoxy, $NH_2$, $NHC_{1\text{-}4}$-alkyl, $N(C_{1\text{-}4}\text{alkyl})_2$, $C_{3\text{-}4}$alkenyl, $C_{3\text{-}4}$-alkynyl, $C_{3\text{-}4}$alkenyloxy, $C_{3\text{-}4}$-alkynyloxy, or $C_{3\text{-}6}$-cycloalkyl;
$R^2$ is $C_{1\text{-}4}$-alkyl, $C_{1\text{-}4}$-alkoxy or halogen;
$R^3$ is hydrogen or halogen;
$R^4$ is hydrogen, halogen, $C_{1\text{-}4}$-alkyl, or $C_{1\text{-}4}$-alkoxy;
$R^5$ is hydrogen, a phenyl group optionally substituted by one or more substituents selected from $C_{1\text{-}4}$-alkyl, $C_{1\text{-}4}$-alkoxy and halogen moieties, a $C_{1\text{-}12}$alkyl group optionally substituted by one or more halogen atoms, a $C_{3\text{-}7}$-cycloalkyl, phenylphenyl or phenoxyphenyl group, a $C_{2\text{-}6}$-alkenyl or $C_{2\text{-}6}$-alkynyl group each optionally substituted by a phenyl group, or a naphthyl or $C_{5\text{-}8}$-cycloalkenyl group;
X is a single bond, $-O-$, $-S(O)_p-$, $-N=N-$, $-CHR^9O-$, $-OCHR^9-$, $-CHR^9S(O)_p-$, $-S(O)_pCHR^9-$, $-(CH_2)_n-$, $-HC=CH-$, or $-C\equiv C-$;
$R^6$ is $C_{1\text{-}4}$-alkyl, $C_{3\text{-}7}$-cycloalkyl, benzyl, $C_{3\text{-}4}$-alkenyl or $C_{3\text{-}4}$-alkynyl;
$R^7$ is $C_{1\text{-}4}$-alkyl;
$R^8$ is hydrogen, $C_{1\text{-}4}$-alkyl or $C_{1\text{-}4}$-alkoxy;
$R^9$ is hydrogen or $C_{1\text{-}4}$-alkyl;
p is 0, 1, or 2; and
n is an integer from 1 to 10.
by reacting a benzophenone of formula II $$\underset{B}{\overset{A}{>}}CO \qquad (II)$$

in which A and B have the meanings given above, with an acetamide of formula III

CH$_3$COQ  (III)

in which Q has the meaning given above, in the presence of an alkali metal tertiary alcoholate characterized in that the reaction is carried out additionally in the presence of an alkali metal mono-alkyl carbonate.

The alkali metal mono-alkyl carbonate may be a carbonic acid half ester salt of any alcohol but normally the alcohol employed will be the same as that used in the alkali metal tertiary alcoholate. Good results have been obtained with those alcoholates and carbonates derived from tertiary alcohols of formula IV (R)$_3$C-OH  (IV)

wherein each R is independently an alkyl group of 1 to 4 carbon atoms.

Preferably two of the groups R are methyl groups and the remaining R is a methyl, ethyl, propyl or butyl group. Preferred alcohols are butyl and amyl alcohol. The alkali metal may be any alkali metal, but preferably it is the same as that used in the alkali metal alcoholate and this is conveniently sodium or potassium.

The alkali metal mono-alkyl carbonate may be prepared in situ or added as such and may be prepared by known methods, e.g. by reaction of carbon dioxide with an alkali metal alcoholate in the presence of an inert solvent. In practice, it is convenient in the process according to the invention if, firstly, a portion of the alkali metal tertiary alcoholate used for the process is reacted with carbon dioxide in an inert solvent to produce the desired carbonate. To this is then added the remaining portion of the alcoholate and the benzophenone and acetamide reactants.

The process according to the invention may be carried out in the presence of inert solvents such as toluene, benzene, diethyl ether, diglyme, tetrahydrofuran, and N,N-dimethyl formamide. According to the reactivity of the components, the reaction may be carried out with cooling, at room temperature or at elevated temperature up to the reflux temperature of the reaction mixture. Generally, the reaction takes place at a temperature in the range from 10° C. to 150° C. It is advantageous to remove the alcohol which is formed in the course of reaction by simultaneous azeotropic distillation. An overall excess of the alkali metal alcoholate (preferably 1.5 - 2 fold) and/or an excess of the acetamide is advantageous. The latter can be recovered and fed into the reaction again. The reaction may also be carried out in the presence of an excess of the alkali metal mono-alkyl carbonate.

The process according to the invention may be used to prepare all the compounds of general formula I but it is particularly useful for compounds of formula I wherein: in group A:

$R^1$ is $C_{1-4}$-alkoxy (e.g. methoxy or ethoxy), $C_{1-4}$-alkyl (e.g. methyl, ethyl or propyl), or amino;

$R^2$ is $C_{1-4}$-alkoxy (e.g. methoxy or ethoxy), $C_{1-4}$-alkyl (e.g. methyl, ethyl or propyl), or halogen; and $R^3$ is hydrogen or halogen;

in group B:

$R^4$ is hydrogen or halogen;

$R^5$ is hydrogen, phenyl or halophenyl (e.g. 4-halophenyl); and

X is a single bond or —O— and Q represents a morpholine group wherein $R^8$ and $R^9$ are both hydrogen.

The halogen or halo-substituent may be a fluorine, chlorine, bromine or iodine atom but is preferably a chlorine or bromine atom.

In the group A, the substitution in the phenyl ring is preferably in the 3 and 4 positions or in the 3,4 and 5 positions, particularly preferred examples of such substitution being 3,4-dimethoxy, 3-ethoxy-4-methoxy, 3-chloro-4-methoxy, 3-bromo-4-methoxy, 3-methyl-4-methoxy, 3-ethyl-4-methoxy, 3-propyl-4-methoxy, 3,4-dimethyl, 3-amino-4-methoxy, 3,5-dichloro-4-amino and 3-methoxy-4-methyl. Of these, 3,4-dimethoxy substitution of the phenyl ring is especially preferred.

A particularly preferred compound of formula I is 3-(4-chlorophenyl)-3-(3,4-dimethoxyphenyl) acrylic acid morpholide.

The process according to the invention normally yields mixtures of cis and trans isomers of 3,3-diphenylacrylic acid amides and these mixtures may, if desired, be separated or converted into the individual cis or trans isomer. The mixture may also be converted into cis-rich or trans-rich mixtures.

The process according to the invention is further illustrated by the following examples.

EXAMPLE 1

3-(4-Chlorophenyl)-3-(3,4-dimethoxyphenyl)acrylic acid morpholide

Sodium hydride (with 20% of paraffin oil; 7.5g, 250 mmol) was stirred with anhydrous xylene (250 ml) at 100° C and tert.-amyl alcohol (23.14 g, 262.5 mmol) was added dropwise over a period of 30 minutes. As soon as the solution was clear, it was cooled to 70° C. and divided into two parts. Into one part of the solution (107 g, corresponding to 110 mmol of sodium tert.-amylate) carbon dioxide was passed with vigorous stirring, whilst the exothermic reaction was kept at 70° C. by slight cooling. The excess carbon dioxide was removed with a stream of dry nitrogen whilst heating to 100°C. for 10 minutes. After that the remaining part of the original solution (137 g, corresponding to 140 mmol of sodium tert.-amylate), 4-chloro-3',4'-dimethoxy benzophenone (27.67 g, 100 mmol) and acetyl morpholine (18.08 g, 140 mmol) were added and the reaction mixture was refluxed for 4 hours with stirring. The tertiary amyl alcohol produced was simultaneously removed by azeotropic distillation (approx 50 ml of distillate,. Finally, the mixture was cooled to 80° C., carbon dioxide was passed through for 30 min, the hot solution was washed with water (2×50 ml) and dried. The xylene was removed on a rotary evaporator and the residue vigorously stirred with diisopropyl ether (100 ml) under reflux whereupon solid product was obtained which was recovered by suction after cooling, washed with diisopropyl ether and dried.

Yield: 32.5 g with a purity of 93.5%, (corresponding to 82.2% of theoretical yield).

mp: 133°–150 ° C.

Isomer ratio: E/Z =45:55.

COMPARATIVE EXAMPLE 3-(4-chlorophenyl)-3-(3,4-dimethoxyphenyl)acrylic acid morpholide The preparation was performed as described above with the exception that no alkali metal mono-alkyl carbonate was present during the reaction.

Yield: 58.7% of theoretical, product purity: 89.6%.

We claim:

1. A process for the preparation of a 3,3-diphenylacrylic acid amide of general formula I

wherein

A represents

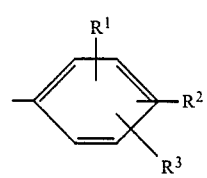

B represents

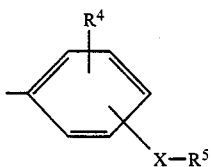

Q represents

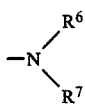

or

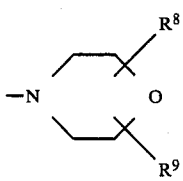

in which
R$^1$ is C$_{1-4}$-alkyl, C$_{1-4}$-alkoxy, NH$_2$, NHC$_{1-4}$-alkyl, N(C$_{1-4}$alkyl)$_2$, C$_{3-4}$-alkenyl, C$_{3-4}$-alkynyl, C$_{3-4}$alkenyloxy, C$_{3-4}$-alkynyloxy, or C$_{3-6}$-cycloalkyl;
R$^2$ is C$_{1-4}$-alkyl, C$_{1-4}$-alkoxy or halogen;
R$^3$ is hydrogen or halogen;
R$^4$ is hydrogen, halogen, C$_{1-4}$-alkyl, or C$_{1-4}$-alkoxy;
R$^5$ is hydrogen, a phenyl group optionally substituted by one or more substituents selected from C$_{1-4}$-alkyl, C$_{1-4}$-alkoxy and halogen moieties, a C$_{1-12}$alkyl group optionally substituted by one or more halogen atoms, a C$_{3-7}$-cycloalkyl, phenylphenyl or phenoxlphenyl group, a C$_{2-6}$-alkenyl or C$_{2-6}$-alkynyl group each optionally substituted by a phenyl group, or a naphthyl or C$_{5-8}$-cycloalkenyl group;
X is a single bond, —O—, —S(O)$_p$—, —N=N—, —CHR$^9$O—, —OCHR$^9$—, —CHR$^9$S(O)—, —S(O)$_p$—CHR$^9$—, —(CH$_2$)$_n$—, —HC=CH—, or —C≡C—;
R$^6$ is C$_{1-4}$-alkyl, C$_{3-7}$-cycloalkyl, benzyl, C$_{3-4}$-alkenyl or C$_{3-4}$-alkynyl;
R$^7$ is C$_{1-4}$-alkyl;
R$^8$ is hydrogen, C$_{1-4}$-alkyl or C$_{1-4}$-alkoxy;
R$^9$ is hydrogen or C$_{1-4}$-alkyl;
p is 0, 1, or 2; and
n is an integer from 1 to 10.
by reacting a benzophenone of formula II

in which A and B have the meanings given above, with an acetamide of formula III
CH$_3$COQ  (III)

in which Q has the meaning given above, in the presence of an alkali metal tertiary alcoholate characterised in that the reaction is carried out additionally in the presence of an alkali metal mono-alkyl carbonate.

2. A process according to claim 1 characterised in that the alkali metal mono-alkyl carbonate is obtained from the reaction of an alkali metal tertiary alcoholate with carbon dioxide in the presence an inert solvent.

3. A process according to claim 1 or 2 characterised in that the alkali metal tertiary alcoholate and the alkali metal mono-alkyl carbonate are derived from an alcohol of general formula IV
(R)$_3$C-OH  (IV)

wherein each R is independently an alkyl group of 1 to 4 carbon atoms.

4. A process according to claim 3 characterised in that the alkali metal is sodium or potassium.

5. A process according to claim 4 characterised in that excess alkali metal alcoholate is present.

6. A process according to claim 4 characterized in that an excess of the alkali metal mono-alkyl carbonate is present.

7. A process according to claim 1 characterized in that the acetamide of formula III is present in excess.

8. A process according to claim 1 characterized in that alcohol is formed and in the course of the reaction is removed by azeotropic distillation.

9. A process according to claim 1 characterized in that the reaction temperature is in the range from 10° C. to 150° C.

* * * * *

UNITED STATES PATENT AND TRADEMARK OFFICE
CERTIFICATE OF CORRECTION

PATENT NO. : 4,912,217

DATED : March 27, 1990

INVENTOR(S) : Jurgen Curtze et al

It is certified that error appears in the above-identified patent and that said Letters Patent is hereby corrected as shown below:

Claim 1 (column 5, line 39), "phenoxylphenyl" should be --phenoxyphenyl--.

Claim 1 (column 5, line 43), "$-CHR^9S(O)-$" should be -- $-CHR^9S(O)_p-$ --.

Claim 1 (column 6, line 2), "$^9$" should be --$R^9$--.

Signed and Sealed this

Sixteenth Day of April, 1991

Attest:

HARRY F. MANBECK, JR.

Attesting Officer

Commissioner of Patents and Trademarks